(12) United States Patent
Azar et al.

(10) Patent No.: US 6,290,496 B1
(45) Date of Patent: Sep. 18, 2001

(54) APPARATUS AND METHOD FOR PHOTOTHERMAL DESTRUCTION OF ORAL BACTERIA

(75) Inventors: Zion Azar, Shoham; Pinchas Shalev, Kfar-Saba, both of (IL)

(73) Assignee: Radiance Inc., Orangeburg, NY (US)

( * ) Notice: Subject to any disclaimer, the term of this patent is extended or adjusted under 35 U.S.C. 154(b) by 0 days.

(21) Appl. No.: 09/255,273

(22) Filed: Feb. 23, 1999

Related U.S. Application Data

(63) Continuation of application No. PCT/IL99/00030, filed on Jan. 17, 1999.

(30) Foreign Application Priority Data

Feb. 24, 1998 (IL) ............................................................ 123437

(51) Int. Cl.[7] ............................................................... A61C 5/00
(52) U.S. Cl. ............................. 433/29; 433/216; 362/804; 132/323
(58) Field of Search .............................. 433/29, 216, 215, 433/229; 362/804; 132/323

(56) References Cited

U.S. PATENT DOCUMENTS

| | | |
|---|---|---|
| 3,261,978 | 7/1966 | Brenman . |
| 4,431,628 * | 2/1984 | Gaffar ................................ 424/7.1 |
| 4,779,173 * | 10/1988 | Carr et al. ............................ 362/109 |
| 4,784,135 | 11/1988 | Blum et al. . |
| 4,951,663 * | 8/1990 | L'Esperance, Jr. . |
| 5,030,090 | 7/1991 | Maeda et al. . |
| 5,160,194 * | 11/1992 | Feldman .............................. 362/109 |
| 5,306,143 * | 4/1994 | Levy ..................................... 433/29 |
| 5,611,793 | 3/1997 | Wilson et al. . |
| 5,624,432 * | 4/1997 | Angelchik .............................. 606/2 |
| 5,658,148 | 8/1997 | Neuberger et al. . |
| 5,813,855 * | 9/1998 | Crisio, Jr. ............................. 433/29 |
| 5,879,159 * | 3/1999 | Cipolla ................................. 433/29 |
| 5,894,620 * | 4/1999 | Polaert et al. ........................ 433/29 |
| 5,975,895 * | 11/1999 | Sullivan ............................... 433/29 |

FOREIGN PATENT DOCUMENTS

| | | |
|---|---|---|
| 29517758 | 2/1996 | (DE) . |
| 0 593 375 A1 | 4/1994 | (EP) . |
| 0 724 894 A3 | 8/1996 | (EP) . |
| WO 98/58595 | 12/1998 | (WO) . |

* cited by examiner

*Primary Examiner*—Ralph A. Lewis
(74) *Attorney, Agent, or Firm*—Fenster & Company, Patent Attorneys Ltd.

(57) ABSTRACT

Oral hygiene apparatus for destroying sensitized oral bacteria, comprising:
- an incoherent light source; and
- a light directing member, adapted for directing light from light source and onto at least part of a surface of at least one tooth within an oral cavity.

34 Claims, 6 Drawing Sheets

APPARATUS AND METHOD FOR PHOTOTHERMAL DESTRUCTION OF ORAL BACTERIA

RELATED APPLICATION

This application is a continuation of PCT Application No. PCT/IL99/00030, filed Jan. 17, 1999, which designated the US.

FIELD OF THE INVENTION

The present invention relates generally to the field of oral hygiene and more particularly to devices and methods for selective photo-thermal destruction of oral bacteria.

BACKGROUND OF THE INVENTION

Various forms of periodontal disease in humans are caused by oral bacteria. Oral bacteria create plaque, a sticky, colorless film of bacteria that constantly forms on the surface of teeth and may lead to periodontal diseases. Plaque, if allowed to stay on the tooth's surface will eventually lead to gingival irritation also known as gingivitis, which may be accompanied by gum swelling, bleeding and by fibrous enlargement of the gingiva.

The plaque forming bacteria create toxins which irritate the gums and result in breakdown of the attachment of gum tissues to teeth. Over time, these toxins can destroy gum tissues, allowing the infection to progress to bone loss.

Plaque that is not timely removed can combine with other materials and harden into a rough, porous deposit called calculus or scale. If the plaque and scale builds up and are not removed by professional cleaning, the gums will start to move away from the teeth. This is the start of periodontal gum disease. Pockets form between the teeth and gums. If the gums are allowed deteriorate further, the gums recede and the bone and other supporting tissues around the teeth start deteriorating and the teeth may eventually become loose.

Calculus on the tooth's surface, above the gum-line, does not contribute to periodontal diseases. However, calculus on the root surface, below the gums, makes removal of new plaque and bacteria more difficult. Unlike plaque, which can be removed by tooth brushing, calculus must be removed by a dentist or dental hygienist.

Prevention and treatment of periodontal gum disease must be based to a large extent on the control of bacterial plaque. This requires a considerable effort on the patient's part. In addition, routine professional oral hygiene techniques, through professional cleaning of the teeth and frequent reassessment of the patient's periodontal tissues to provide early detection and treatment of new or reoccurring abnormalities or of destruction of supporting periodontal tissues.

By far the most important aspect of controlling periodontal diseases is the practicing of daily oral hygiene techniques that needs to be initiated at pre-adolescence and carried on for the rest of the patient's life. Daily maintenance schedules ideally require full patient's compliance with instructions and an ideal tooth cleaning technique. Far too often, token attempts at dental bacterial control are inadequate and unsuccessful in one or more sites of the dentition leading to inflammatory changes at these sites and further loss of periodontal attachment.

Products sold for the prevention of periodontal diseases include toothpaste, mouth rinsing solutions, Manual toothbrushes, dental floss and powered toothbrushes and oral irrigators.

Chemical antibacterial agents are increasingly being used in prophylactic and therapeutic regimes for plaque-related diseases. As these agents can be rendered ineffective by the development of resistance in the target organisms there is a need to develop alternative anti-microbial treatments. Light from high-power lasers is known to be bactericidal and investigations have shown that it is effective against organisms implicated in carries and inflammatory periodontal diseases. However, the adverse effects of such light on dental hard tissues argues against its use solely as an antibacterial agent.

U.S. Pat. No. 4,784,135 to Blum et al. discloses a method for treating tooth decay, by far UV radiation generated by an argon fluoride (ArF) laser, which is based on ablative photo-decomposition of organic biological material. No staining of the material is disclosed.

U.S. Pat. No. 5,658,148 to Neuberger et al. discloses a method and a device for cleaning teeth by a low power diode laser applying the principle of photodynamic therapy. This method is based on using a photosensitizer compound. The photosensitizer compound produces singlet oxygen upon irradiation by the laser light. The singlet oxygen thus produced destroys oral bacteria.

U.S. Pat. No. 5,611,793 to Wilson discloses a method of disinfecting or sterilizing tissues, wounds or lesions of the oral cavity. The method comprises applying a photosensitizing compound to the tissues and irradiating the tissues with laser light at a wavelength absorbed by the photosensitizing compound. The helium-neon laser or the gallium aluminum arsenide diode laser used by Wilson are expensive and may not be suitable for home use.

There is a widely recognized need for a simple, inexpensive and selective method for killing oral bacteria which is suitable for home use.

SUMMARY OF THE INVENTION

It is therefore an object of some preferred embodiments of the present invention to provide a device and method for destroying oral bacteria.

An aspect of some preferred embodiments of the present invention involves the pre-staining of the bacteria using bacterial selective dyes or stains.

An aspect of some preferred embodiments of the present invention involves the use of incoherent broad band light for irradiating the preferably pre-stained bacteria.

As aspect of some preferred embodiments of the invention involves a dentifrice containing a bacterial stain. This dentifrice is preferably used to stain the bacteria during normal brushing so that they can be destroyed.

There is thus provided, in accordance with a preferred embodiment of the invention, oral hygiene apparatus for destroying sensitized oral bacteria, comprising:

an incoherent light source; and a light directing member, adapted for directing light from said light source onto at least part of a surface of at least one tooth within an oral cavity.

Preferably, the light directing member comprises a light guide removably coupled to a housing containing the light source.

Preferably, the light directing member comprises a reflective layer coating light passage. Preferably, the reflective layer coated light passage comprises a hollow passage whose radial extent is defined by a light reflecting surface.

In a preferred embodiment of the invention, the light guide comprises an elongated member, having at least one peripheral surface uncoated by a reflecting material, said light guide directing light entering it at one end by internal reflection from said at least one peripheral surface to a second end.

In a preferred embodiment of the invention, the incoherent light source includes a lamp, a reflector which directs at least part of the light produced by said lamp to said light directing member. Preferably, the lamp is an arc discharge lamp or a flash lamp. Preferably, reflector is a parabolic reflector, a spherical reflector, a quasi-spherical reflector or an ellipsoidal reflector.

In a preferred embodiment of the invention the light source further includes at lease one lens disposed between said flash lamp and said light directing member for directing light onto said light directing member.

Preferably, the apparatus includes at least one filter which passes light to which said bacteria has been sensitized. Preferably, the at least one filter substantially blocks light at wavelengths at which oxyhemoglobin absorbs substantial energy.

In a preferred embodiment of the invention, the light is directed to said tooth surface from an exit port of the light directing member.

In a preferred embodiment of the invention, the apparatus a tooth brush like member adjacent to or surrounding said exit port. Preferably, the tooth brush like member comprises a plurality of bristle like members arranged peripherally around said exit port to enable said light exiting said port to reach said at least part of a surface of at least one tooth within said oral cavity while teeth are being brushed by said tooth brush like member.

In a preferred embodiment of the invention the apparatus includes a plurality of bristles coupled to said light directing member such that a first end of said plurality of bristles is optically coupled to said second end of said light guide and a second end of each of said plurality of bristles extends out of said terminal part for directing at least part of said light onto said at least part of said surface of said at least one tooth within said oral cavity.

In a preferred embodiment of the invention the apparatus includes a dental floss like member optically coupled to said incoherent light source which member emits said light along its length.

In a preferred embodiment of the invention the apparatus includes a power source that powers the incoherent light source and a controller that controls said light source. Preferably, the power source is a battery and said incoherent light source, said battery and said controller are mounted within a common housing.

In a preferred embodiment of the invention, the light directing member is easily separated from the light source and wherein the light directing member is disposable.

In a preferred embodiment of the invention, the light source is a pulsed light source.

There is further provided, in accordance with a preferred embodiment of the invention, a method for selective photothermal destruction of bacteria, the method comprising:

selectively staining at least some bacteria by application of a suitable selective bacterial stain; and exposing at least some of said stained bacteria after said step of selectively staining to incoherent light, to photothermally coagulate said bacteria.

Preferably the incoherent light is band limited to exclude a portion of said light having wavelengths which are substantially absorbed by oxyhemoglobin. Preferably, the incoherent broad band light is pulsed.

In a preferred embodiment of the invention, the pulsed incoherent broad band light has a frequency of pulsing in the range of 0.5–50 pulses per second, a pulse duration in the range of 0.1–10 milliseconds and an energy density in the range of 0.1–10 joule/cm$^2$.

Preferably, the selective bacterial stain has at least one substantial light absorption peak which has no substantial overlap with the major peaks of light absorption of oxyhemoglobin.

Preferably, exposing comprises:

generating at least one pulse of light to exclude a substantial portion of said at least one pulse of light, said portion having wavelengths which are substantially absorbed by oxyhemoglobin, to convert said at least one pulse of light into at least one band-limited light pulse; and directing said at least one band-limited light pulse onto said bacteria to photothermally coagulate said bacteria.

In a preferred embodiment of the invention, the bacteria are oral bacteria. Preferably, the bacteria are situated in the oral cavity.

There is further provided, in accordance with a preferred embodiment of the invention, a dentifrice including a stain for bacteria in a concentration sufficient to stain at least some bacteria remaining in the mouth after tooth brushing with the dentifrice. Preferably, bacteria stained with said stain have a substantial absorption peak at a wavelength for which oxyhemoglobin does not have such an absorption peak. Preferably, the stain comprises E-127 (Erythrosin-B), preferably in a weight percentage of 0.1%–1%.

There is further provided, in accordance with a preferred embodiment of the invention, an oral hygiene kit comprising:

a dentifrice according to the invention; and an oral hygiene apparatus comprising:

an light source which generates radiation which is absorbed by the stain; and a light directing member, adapted for directing light from said light source onto at least part of a surface of at least one tooth within an oral cavity.

Preferably, the oral hygiene apparatus is constructed according to the invention.

BRIEF DESCRIPTION OF THE DRAWINGS

The invention will be more clearly understood by the following description of preferred embodiments thereof, herein described, by way of example only, with reference to the accompanying drawings, in which like components are designated by like reference numerals wherein.

DETAILED DESCRIPTION OF THE INVENTION

Preferred embodiments of the present invention are based on the use of incoherent broad band light for the selective photothermal destruction of selectively stained oral bacteria within dental plaque. The bacteria are stained preferably by applying a liquid or paste like formulation containing a bacterial selective dye within the oral cavity preferably followed by rinsing the oral cavity to wash out excess dye. The bacteria within the dental plaque are thus selectively stained by the dye.

The inventors of the present invention have noticed that when irradiated with broad band incoherent light, the stained bacteria within the plaque absorb more light than nearby non stained tissues, leading to a temperature increase of the stained bacteria and to their destruction by coagulation. However, broad band light including light having wavelengths in the range substantially absorbable by oxyhemoglobin may be absorbed by the oxyhemoglobin contained within red blood cells of the blood included in blood vessels. This may lead to undesired photothermal coagulation of blood vessels within the oral cavity. To prevent such undesired blood vessel coagulation the broad band light is preferably filtered to exclude a substantial portion of the light having wavelengths which are substantially absorbed by oxyhemoglobin. Thus the filtered light is band limited. The main absorption peak of oxyhemoglobin is at a wavelength of 418 nm with an absorption bandwidth of approximately 60 nm around this main peak. Oxyhemoglobin also has secondary absorption peaks at 542 nm and 577 nm with an overall bandwidth of approximately 100 nm around these peaks.

Optimally, band limiting of the broad band light is coupled with the selection of specifically selected stains or dyes which selectively stain bacteria within dental plaque and which have at least one major absorption peak at least a portion of which has no substantial overlap with the major peaks of light absorption of oxyhemoglobin. When the broadband irradiation is filtered to exclude the absorption peaks of the oxyhemoglobin, the stains or dyes absorb enough light energy from the band limited light irradiating them to ensure efficient photothermal destruction of the stained bacteria, without damage to the oxyhemoglobin.

An example of such a dye suitable for selective photothermal destruction of oral plaque forming bacteria is the topical solution of erythrosin B, commercially available from TRISA AG, Switzerland. The oral bacteria may be stained by putting 3–5 drops of the topical solution of erythrosin B under the tongue and rinsing the teeth with the dye solution for approximately 30 seconds, followed by washing the mouth. The surfaces of the teeth that have bacterial plaque on them are thus stained red.

Figure 1:
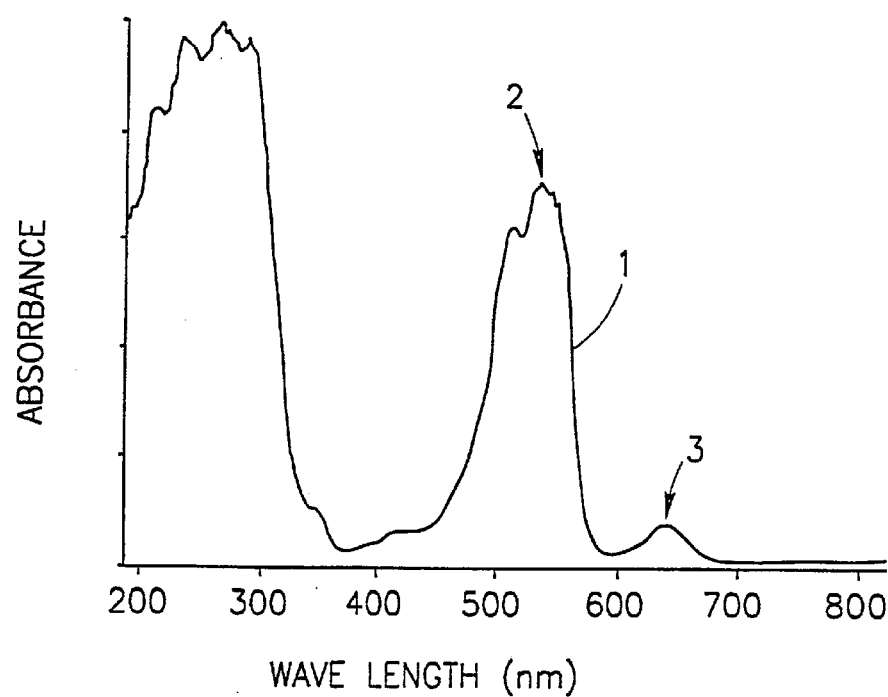
FIG. 1 is a schematic graph illustrating the absorption spectrum of an aqueous solution erythrosin B.

Reference is now made to FIG. 1 which is a schematic graph illustrating the absorption spectrum of an aqueous solution of erythrosin B. The horizontal axis represents the wavelength in nanometers and the vertical axis represents the absorbance in arbitrary units. The curve labeled 1 represents the absorption spectrum of erythrosin B. The curve has a main absorption peak 2 at a wavelength of approximately 542 nm and a secondary absorption peak 3 at a wavelength of approximately 638 nm.

It is noted that the main absorption peak 2 is within the absorption region of oxyhemoglobin. However, peak 3 is outside the absorbance peaks of oxyhemoglobin.

Another example of a dye suitable for selective photothermal destruction of oral plaque forming bacteria is PLAK-CHEK™, commercially available from Clairol Inc., Conn. USA. The staining method is similar to the method described for erythrosin B hereinabove.

Figure 2:
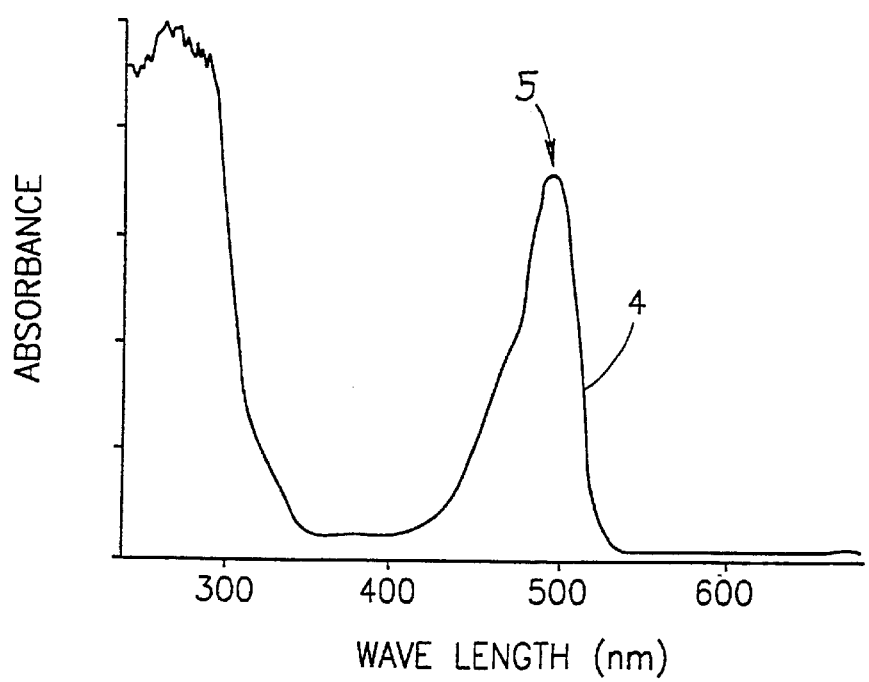
FIG. 2 is a schematic graph illustrating the absorption spectrum of the commercially available stain PLAK CHEK™.

Reference is now made to FIG. 2 which is a schematic graph illustrating the absorption spectrum of the commercially available stain PLAK-CHEK™.

The horizontal axis represents the wavelength in nanometers and the vertical axis represents the absorbance in arbitrary units. The curve labeled 4 represents the absorption spectrum of the PLAK-CHEK™ solution. The curve has a main absorbance peak 5 at a wavelength of approximately 494 nm. The main absorbance peak 5 has a bandwidth of approximately 40 nm. Thus, PLAK-CHEK™ may be a better stain than erythrosin B since its main absorption peak 5 does not substantially overlap the absorption peak of oxyhemoglobin.

It is noted that, since both of the staining dyes disclosed hereinabove have a relatively broad bandwidth of absorption, using a non coherent light source having a suitably broad bandwidth corresponding to the full bandwidth of the main absorption peak of the dye is preferable to using a narrow bandwidth laser. Thus, such a narrow bandwidth laser will be less efficient for photothermal heating of these dyes than a non coherent light source.

Figure 3:
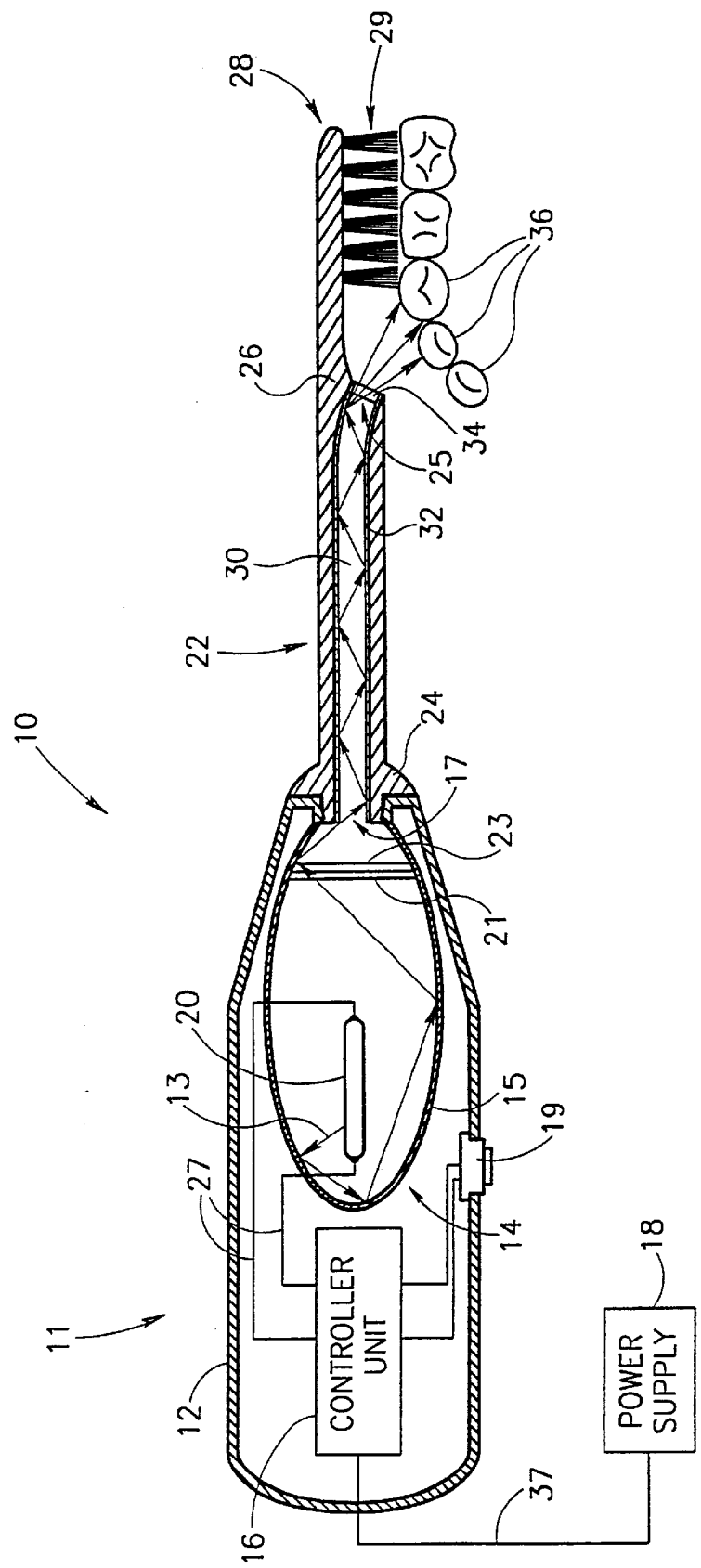
FIG. 3 is a schematic part block diagram part cross sectional view of a device for selective photothermal destruction of oral bacteria, in accordance with a preferred embodiment of the present invention.

Reference is now made to FIG. 3 which is a schematic part block diagram part cross sectional view of a device for selective photothermal destruction of oral bacteria, in accordance with a preferred embodiment of the present invention. Device 10 includes a handle 11 having a housing 12. Housing 12 is preferably formed of a thermally and electrically insulating material such as plastic or the like. Device 10 also includes an incoherent light source 14 and a controller unit 16 preferably disposed within housing 12 and attached thereto. Incoherent light source 14 preferably includes a reflector 15 and a lamp 20 disposed within the reflector. Reflector 15 is preferably reflective and is made from a reflective metal shell such as aluminum or any other suitable highly reflective metal. Alternatively, reflector 15 is formed of plastic or any other suitable material coated, on its internal surface, by a light reflecting coating. The reflector or reflecting surface faces lamp 20 and reflects light produced by the lamp. Lamp 20 is preferably electrically connected to controller unit 16 by suitable isolated electrically conductive wires 27. Device 10 further preferably includes a power supply 18 that supplies electrical power to lamp 20 and to the controller unit 16. Power supply 18 is preferably suitably connected to controller unit 16 by a power cable 37 entering housing 12. Alternatively power supply may be attached to the housing.

Power supply 18 may be a direct current (DC) source such as a disposable or a rechargeable battery or any other suitable type of battery. Alternatively, power supply 18 can be an alternating current (AC) operated power supply suitably connected to the mains.

Reflector 15 is preferably shaped as an ellipsoidal reflector and has an opening 17 at it's end which is attached to housing 12. Ellipsoidal reflector 15 has two focal points. Lamp 20 is preferably disposed in the region of the focal point which is distal from opening 17. However, lamp 20 may also be disposed at other regions within reflector 15. Alternatively, opening 17 may be centered about the right focus of the ellipsoid to improve the coupling of the light into the opening. Alternatively or additionally, the reflector may have a different shape that couples the light generated by the lamp into the opening. Alternatively, the reflector may have other shapes such as parabolic, quasi-parabolic, spherical, quasi spherical, quasi-ellipsoidal reflectors or any other suitable shape.

Light source 14 further preferably includes one or more filters 21 and 23 situated between lamp 20 and opening 17 which filters the light produced by the lamp 20 to produce band limited light.

In a preferred embodiment of the invention lamp 20 is an arc discharge lamp such as a flash lamp or any other lamp suitable for producing incoherent broad band light having an energy density sufficient for performing photothermolysis of dye stained bacteria. Preferably, lamp 20 is a xenon flash lamp that has a peak of light emission in the visible part of the spectrum at around 500 nanometers. One suitable lamp is xenon flash lamp model G5109 commercially available from The Electronic Goldmine, Ariz., USA.

When a xenon flash lamp is used and system 10 is designed for use in conjunction with the PLACK CHEK™ stain, filter 21 preferably transmits all wavelengths above 450 nm and blocks all wavelengths below 450 nm and filter 23 preferably transmits all wavelengths below 500 nm and blocks all wavelengths above 500 nm. For example, filters 21 and 23 can be the filters having catalog numbers 450FH-90-25 and 500FL07-25, respectively, commercially available from Andover Corporation, N.H., USA.

Filters 21 and 23 filter the broad band light produced by the xenon lamp to produce incoherent light which is band limited with a bandwidth of approximately 50 nm including the approximate wavelength range of 450–500 nm. This band of wavelengths is outside the absorption bands of oxyhemoglobin and within the main absorption band of the stain.

It is noted that, while the non-limiting examples of filters 21 and 23 disclosed hereinabove are suitable for use in a device designed for being used in conjunction with PLACK CHEK™, other different types of filters having similar absorbance ranges can also be used.

It is further that, if other selective bacterial stains or dyes which are different from the stain PLACK CHEK™ are used, filters 21 and 23 are preferably chosen to pass wavelengths which match the absorbance of the particular stain or dye.

It is still further that, while the filtering of the light of lamp 20 is disclosed as being performed by two distinct filters 21 and 23, it is also possible to use a single optical filter having appropriate band limiting characteristics.

In another example, if the device 10 is used the dye erythrosin B, a single filter can be used to replace filters 21 and 23. The single filter preferably absorbs all the wavelengths below 600 nm and transmit all wavelength above 600 nm. A suitable filter for use with erythrosin B is the filter having a catalog number 600FH90-25 commercially available from Andover Corporation, N.H., USA.

Controller unit 16 controls the energizing of flash lamp 20. Controller unit 16 includes standard electronic circuitry needed to operate the flash lamp 20 such as a triggering unit, a capacitor unit and electronic timing circuitry for timing the frequency of flashing of the lamp 20. A suitable electronic circuit that can be used to construct as the controller unit 16 is the Personal Safety Strobe, Catalogue Number 61-2506, commercially available form Radio Shack, a division of Tandy Corporation, Tex., USA The Personal Safety Strobe circuitry is preferably modified by electrically connecting an electrolytic capacitor having a capacitance of 120 microfarad (rated as 330 volts) in parallel with the capacitor already included in the Personal Safety Probe. The flashing frequency of the modified Personal Safety Strobe is approximately 1 Hz.

It is noted that, The particular circuitry disclosed hereinabove is given by way of example only and that many other types of circuitry known in the art can be used to implement controller unit 16.

Device 10 preferably includes an on-off switch 19 attached to the housing 12 and suitably connected to the controller 16 for starting and stopping the operation of the controller 16. The switch 19 can be any suitable type of switch. It is noted that, while the switch 19 of FIG. 3 is attached to the housing 12, the switch may be attached to the housing 12 or to the power supply or to any other suitable part of the device.

Device 10 further preferably includes a light directing member 22 attached to handle 11 for directing light from the incoherent light source 14 into the oral cavity of a user. In a preferred embodiment of the invention, light directing member 22 of the device 10 is an elongated member made of a thermally insulating material such as plastic or the like. Light directing member 22 has a proximal end 24 preferably detachably attached to housing 12 and a distal end 26 extending distally of the housing 12.

In one preferred embodiment of the invention, light directing member 22 has a hollow passage 30 passing therethrough. Hollow passage 30 has an opening 17 at proximal end 24 of member 22 to receive light from light source 14 and a second opening 25 at distal end 26 of member 22. Opening 25 is preferably closed by an optical window 34 which seals opening 25. Optical window 34 is preferably made from a material which is substantially transparent to the band limited light which passes through filters 21 and 23. For example optical window 34 can be made from a suitable glass or a suitable plastic material or the like. Alternatively, one or both of filters 21 and 23 can be omitted from the light source and placed within the light guide or as a replacement for or as part of window 34.

Optical window 34 prevents any material such as saliva or other liquids or solid materials present in the oral cavity from entering and accumulating in passage 30 and partially or fully blocking the path of the light produced by light source 14 from entering the oral cavity.

It is noted that, while the light directing member preferably includes optical window 34, other embodiments of the present invention are possible which do not include an optical window and opening 25 is uncovered.

Light directing member 22 preferably further includes a layer 32 of light reflecting material attached to the internal surface of passage 30. Layer 32 is preferably made of a light reflecting material such as aluminum or any other metal or material having suitable light reflecting properties. Layer 32 may be formed by deposition thereof on the internal surface of passage 30 or by any other suitable forming or attaching method such as, for example vapor deposition or electroplating methods may be used.

Light reflecting layer 32 forms a light guide which guides the light produced by light source 14 and directs it onto the surfaces of teeth 36 within the oral cavity of the user.

In other preferred embodiments of the invention, the light guide may be any other type of suitable light guide as known in the art. For example, it may be a solid plastic rod coated on its outside with a light reflective coating or cladding. Alternatively, the light may be reflected from the outer surface of the guide by total internal reflection. Other suitable light guides will occur to persons of skill in the art.

Preferably, passage 30 has a circular cross-section. However, the passage 30 may also have an oval cross-section or any other cross section suitable for use in a light guide.

Light directing member 22 further preferably includes a tooth brush member 28 extending from end 26 of light directing member 22. Tooth brush member 28 preferably includes a plurality of bristles 29 for brushing teeth.

It is noted that, while the tooth brush like member 28 is a physical extension of the end 26 of the light directing member 22, it can also be formed as a separate part (not shown) which can be attached to the end 26 by gluing or fusing or by any other suitable attachment means.

When device 10 is used for photothermal destruction of oral bacteria, a user first selectively stains plaque bacteria by using a bacterial selective stain or dye such as PLAK-CHECK™ as described above. The user then holds housing 12 in his hand, switches switch 19 to the "on" position to commence the flashing of flash lamp 20 of light source 14, and inserts brush member 28 into his oral cavity. The user then brushes his teeth using brush member 28. Preferably, flash lamp 20, is flashed at a flashing rate of approximately 1 Hz to 10 Hz, but flashing rates in the range of approximately 0.5–50 Hz may be used. Typically, each light flash has a duration of 0.1 to 10 msec and irradiates the teeth 36 with incoherent band limited light having an energy density of approximately 0.1–10 Joule/cm$^2$, thereby heating stained bacteria to the temperature of coagulation. Using energy densities within this range, even a single flash can effectively cause photothermal heating and coagulation of selectively stained plaque bacteria.

Light rays produced by flash lamp 20 such as light ray 13 are reflected by reflector 15, directed towards filters 21 and 23 to be filtered thereby. The filtered light rays are directed within the light guide by multiple reflections from the reflecting layer 32 to exit from the exit 25. The filtered light rays are directed towards the surface of teeth 36 for coagulating stained plaque bacteria by photothermal heating.

The frequency of flashing of the lamp 20 by the electronic timer circuitry may be factory preset so as to take into account the typical parameters of the movements of the brush member 28 over the teeth during brushing of teeth by the user and to provide a sufficient irradiation of the surfaces of the teeth within the oral cavity of the user for efficient photothermal destruction of dental plaque bacteria.

After the user finishes the photothermal coagulation procedure, the user switches off the flashing of the flash lamp 20 by switching the switch 19 to the "off" position. If desired, the user may then apply a tooth paste to the bristles 29 of the tooth brush like member 28 and proceed to brush his teeth normally.

Alternatively, the person first brushes his teeth normally, using ordinary toothpaste or other dentifrice. The bacteria is then stained and the above irradiation procedure is performed.

Alternatively, a toothpaste incorporating a stain as described herein is used for ordinary brushing with the brush member. This brushing will be operative to clean the teeth and to stain any remaining bacteria. The mouth and the toothbrush are then preferably rinsed and the irradiation procedure, as described herein, is performed. In a preferred embodiment of the invention, E-127 red food coloring (Erythrosin-B) in a concentration of 0.1%–1% can be used as the stain. Other suitable stains can also be used.

As may be noted, light directing member 22 and brush member 28 are preferably detachable from handle 11. Thus, a separate directing member may be used for each person using the device. Furthermore, the brush may be replaced from time to time as it becomes used.

Figure 4:
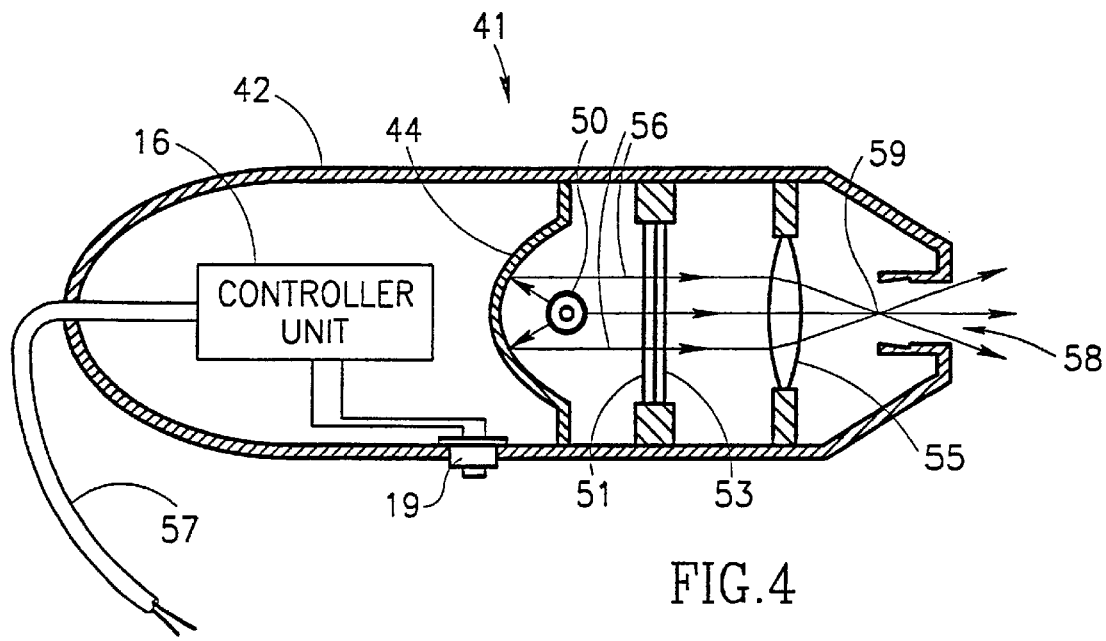
FIG. 4 is a schematic cross sectional view of a hand held part of a device for selective photothermal destruction of oral bacteria, in accordance with another preferred embodiment of the present invention.

Reference is now made to FIG. 4 which is a schematic cross sectional view of a handle 41 of a device for selective photothermal destruction of oral bacteria, in accordance with another preferred embodiment of the present invention. Handle 41 includes a housing 42 having a recessed opening 58 therein. Handle 41 further includes a controller unit 16 attached to a power supply (not shown) by a suitable power cable 57. Handle 41 also includes switch 19 suitably connected to the controller 16 as disclosed with respect to FIG. 3. Switch 19 is used to turn controller 16 on and off as disclosed for device 10 of FIG. 3. Handle 41 further includes a reflector 44 to reflect light from a lamp 50 to an opening 58. Handle 41 preferably also includes a lens 55 situated between filter 23 and opening 58.

Lamp 50 is similar to lamp 20 of FIG. 3 and is electrically connected to the controller 16 by a conducting wires (not shown for the sake of clarity of illustration). Reflector 44 is made of a light reflecting material such as polished aluminum or any other suitable reflecting material. Alternatively, the reflector 44 may be made of a preferably thermally insulating material such as plastic or the like which is plated or coated by a light reflecting layer made of a suitable reflecting metal such as aluminum, silver or the like. Reflector 44 is preferably a parabolic reflector but can also have a quasi-parabolic, spherical or quasi-spherical shape or any other suitable shape. Light rays 56 produced by the lamp 50 are reflected by the reflector 44, filtered by the filters 21 and 23 as described above and focused by the lens 55 at a point 59 within opening 58.

Handle 41 can be attached to light directing member 22 of FIG. 3 by inserting end 24 of member 22 into opening 58 of handle 41. When switch 19 is switched on, the light produced by lamp 50 and focused at point 59 enters into passage 30 and is directed by the light guide formed from the reflecting layer 32 to exit from the optical window 34 as disclosed above.

Figure 5A:
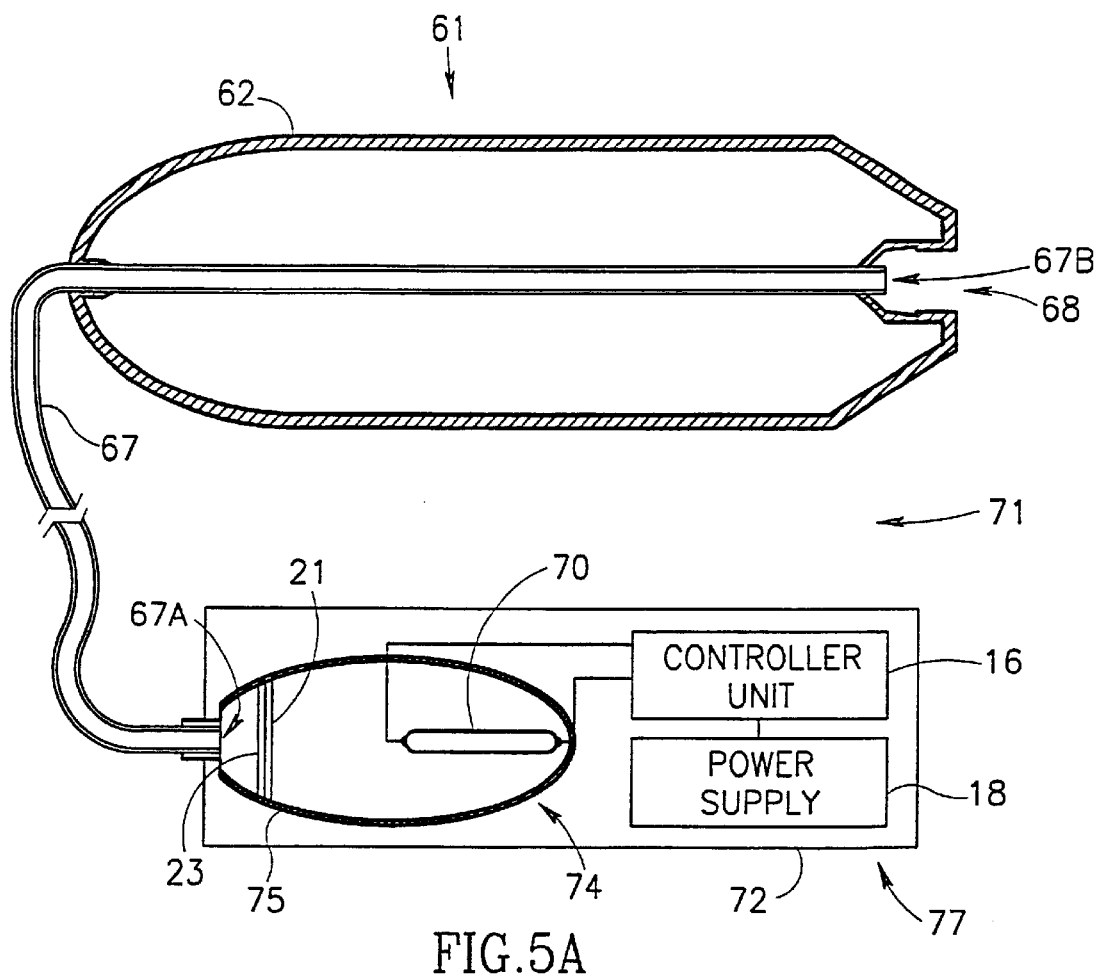
FIG. 5A is a schematic part block diagram part cross sectional view of a device for selective photothermal destruction of oral bacteria having a light source optically coupled to a hand held part by an optical fiber bundle, in accordance with yet another preferred embodiment of the present invention.

Reference is now made to FIG. 5A which is a schematic part block diagram/part cross sectional view of a device 71 for selective photothermal destruction of oral bacteria. Device 71 has a light source optically coupled to a hand held part by an optical fiber bundle 67, in accordance with yet another preferred embodiment of the present invention.

Device 71 includes a handle 61 and a base 77. Handle 61 includes a housing 62 having a recessed opening 68 therein. Handle 61 and the base 77 are optically coupled by flexible optical fiber bundle 67 passing through housing 62 of handle 61 and attached thereto. Base 77 preferably includes a housing 72, a light source 74, a power supply 18 and controller 16 electrically connected to light source 74 to control the energizing of light source 74 by power supply 18. Base 77 also may include a control panel (not shown in FIG. 5A) suitably connected to controller 16 for activation of the controller.

Light source 74 preferably includes a lamp 70 similar to lamp 20 of FIG. 2 and electrically connected to controller 16. Light source 74 preferably also includes a reflector 75 which includes filters 21 and 23 attached thereto as disclosed above. Reflector 75 is made of a light reflective material or is constructed from a thermally insulated material coated with a light reflecting layer as disclosed above. The reflected 75 may be ellipsoidal but may also have other shapes as disclosed above. Optical fiber bundle 67 has a first end 67A and a second end 67B. Light source 74 is optically coupled to first end 67A, by the structure shown or by other suitable means known in the art. Optical fiber bundle 67 passes within housing 62 of handle 61 and end 67B of optical fiber bundle 67 is attached to housing 62 at recessed opening 68 in such a way that it can be optically coupled to the light guide of light directing member 22 of FIG. 3. Thus, light produced by light source 74 enters first end 67A and is directed by the individual optical fibers within optical fiber bundle 67 to exit at second end 67B.

It is noted that end 67B of optical fiber bundle 67 can also be optically coupled to various types of light directing members which are constructed differently from light directing member 22 of FIG. 3 some of which are disclosed below.

Figure 5B:
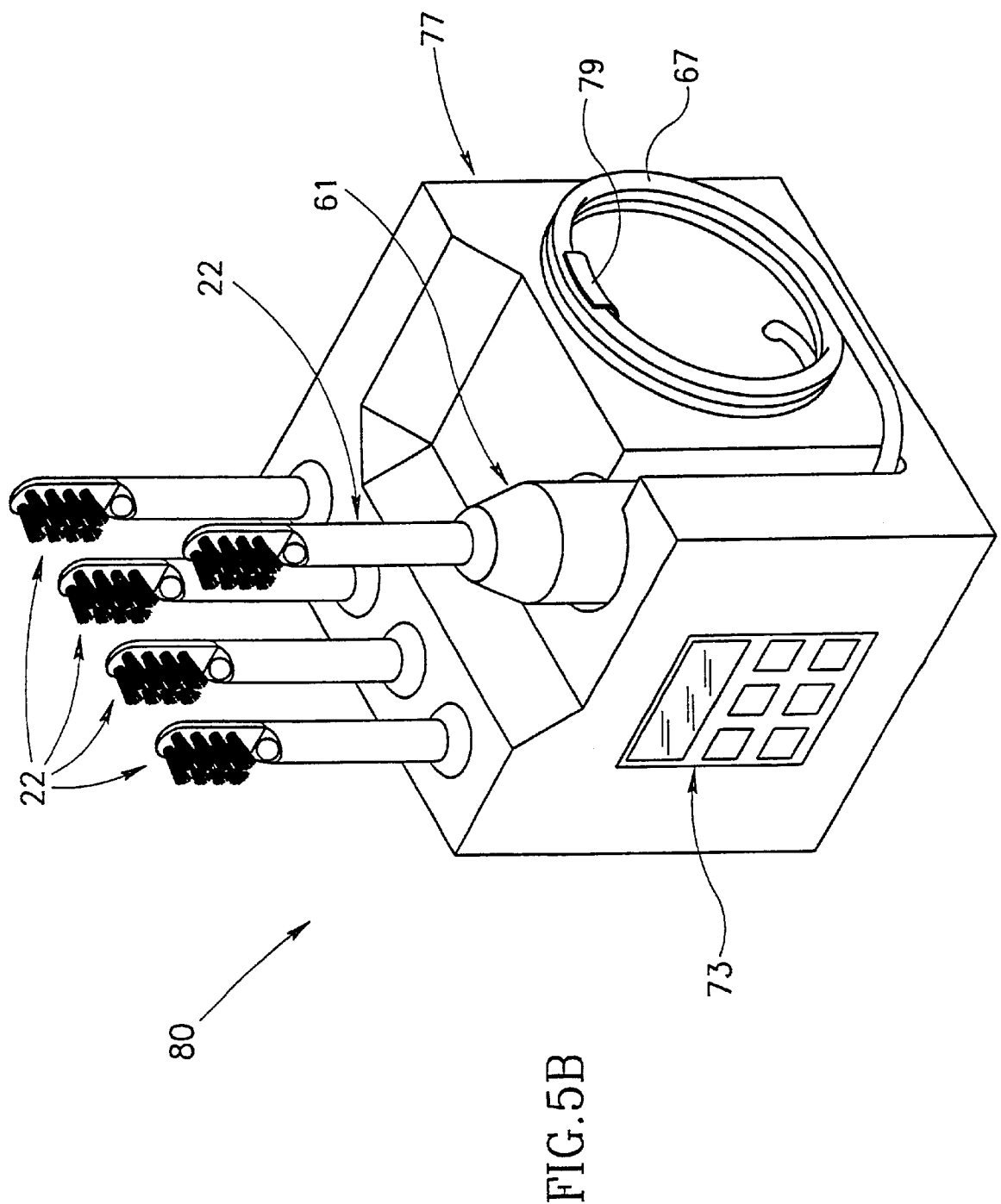
FIG. 5B is an isometric view of a system for selective photothermal destruction of oral bacteria including the device of FIG. 5A and a plurality of the light directing members of the type illustrated in FIG. 3.

Reference is now made to FIG. 5B which is an isometric view of a system 80 for selective photothermal destruction of oral bacteria including the device of FIG. 5A and a plurality of the light directing members of the type illustrated in FIG. 3.

FIG. 5B illustrates base 77 which includes a control panel 73 for activation of controller unit 16 by the user. Base 77 is suitably formed to house handle 61 while it is not being used. Base 77 is also suitably formed to house a plurality of light directing members 22 each of which may be attached to handle 61 for use by a different individual for his own personal use. Optical fiber bundle 67 may be conveniently wound around a member 67 for storage.

Figure 6:
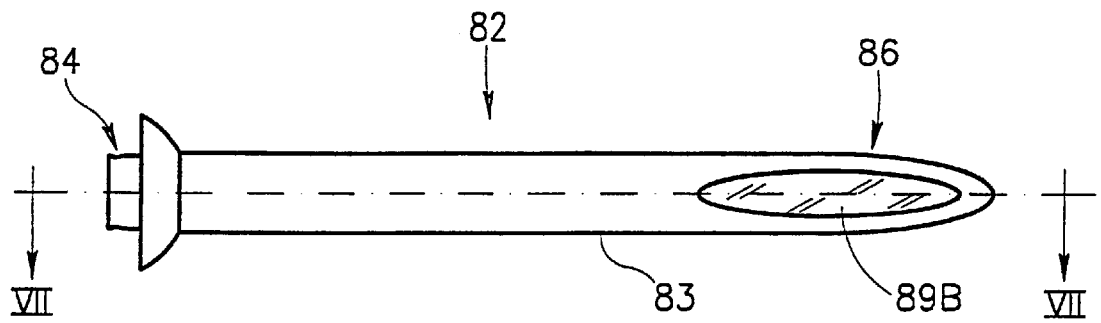
FIG. 6 is an isometric view of a light directing member attachable to the handle of the devices of FIGS. 3, 4 and 5A–5B.
Figure 7:
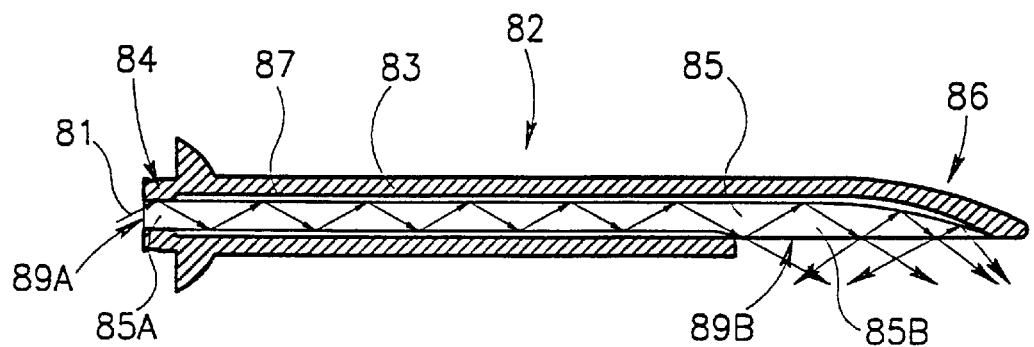
FIG. 7 is a cross sectional view of the light directing member of FIG. 6 taken along the lines VII—VII.

Reference is now made to FIGS. 6 and 7. FIG. 6 is an isometric view of a light directing member 82, in accordance with a preferred embodiment of the invention, attachable to the handle of the devices of FIGS. 3, 4 and 5A–5B. FIG. 7 is a cross sectional view of the light directing member of FIG. 6 taken along the lines VII—VII.

Light directing member 82 is an elongated member having a proximal end 84 and a distal end 86. Proximal end 84 can preferably be detachably attached to any of handles 11, 41 and 61 of FIGS. 3, 4 and 5, respectively. Distal end 86 is insertable into the oral cavity of the user (not shown).

Turning to FIG. 7, the light directing member 82 includes a hollow member 83 preferably made from a thermally insulating and light opaque material such as opaque plastic or the like. Light directing member 82 further includes a light guide 85 having a first end 85A and a second end 85B. First end 85A of light guide 85 is attached to hollow member 83 at proximal end 84 of light directing member 82 and second end 85B of light guide 85 is attached to hollow member 83 at distal end 86 of light directing member 82. Light guide 85 is preferably separated from hollow member 83 by an air gap 87. Preferably, first end 85A of light guide 85 terminates in a flat surface 89A which is suitable for being optically coupled to a light source such as light source 14 of FIG. 3 or to second end 67B of optical fiber bundle 67 of FIG. 5A. Second end 85B of light guide 85 terminates in a flat surface 89B which is suitable for directing the light entering light guide 85 onto the oral cavity of a user.

Light guide 85 is optimally made from a material which is transparent to the bandwidth of the band limited light which is being used for photothermally coagulating the oral bacteria. The transparent material forming light guide 85 has an index of refraction which is higher than the index of refraction of air. A light ray 81 which enters light guide 85 at surface 89A is guided by multiple reflection along light guide 85 towards end 85B of light guide 85 where it exits through surface 89B.

Preferably, light guide 85 is shaped as a rod having a generally circular cross-section and is made from clear polymethylmetacrylate (PMMA), glass or any other optically suitable transparent material. However, light guide 85 may have other different shapes and cross-sections which are suitable for implementing a light guide.

Figure 8:
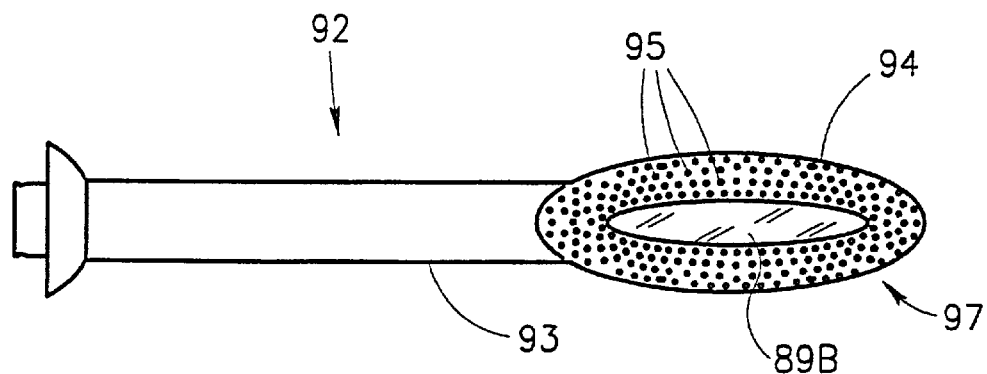
FIG. 8 is a side view of a toothbrush like light delivery member attachable to the handle of the devices of FIGS. 3, 4 and 5, in accordance with another preferred embodiment of the present invention.

Reference is now made to FIG. 8 which is a side view of a toothbrush like light delivery member 92 attached to the handle of the device of FIGS. 3, 4 and 5, in accordance with another preferred embodiment of the present invention. Light directing member 92 is similar to light directing member 82 of FIG. 6 and includes a light guide 83.

However, in contrast to hollow member 83 of FIG. 6, hollow member 93 of light directing member 92 includes a lip 94 extending therefrom and surrounding surface 89B. A plurality of bristles 95 are attached to lip 94 and extend from lip 94 in a direction is generally perpendicular to the surface of the 94 forming a tooth brush like member 97 at the end of light directing member 92. When the light directing member 92 is attached to a handle such as, for example, handle 11 or 41 or 61 of FIGS. 3, 4 and 5A, respectively, and teeth within the oral cavity of a user are brushed by tooth brush like member 97, the light which exits from surface 89B is not blocked by bristles 95 and illuminates part of the surface of the teeth which lie underneath tooth brush like member 97.

It is noted that, while light can be directed onto the surfaces of teeth as discussed hereinabove for the light directing members 22, 82 and 92, other methods for directing light can be used.

Figure 9:
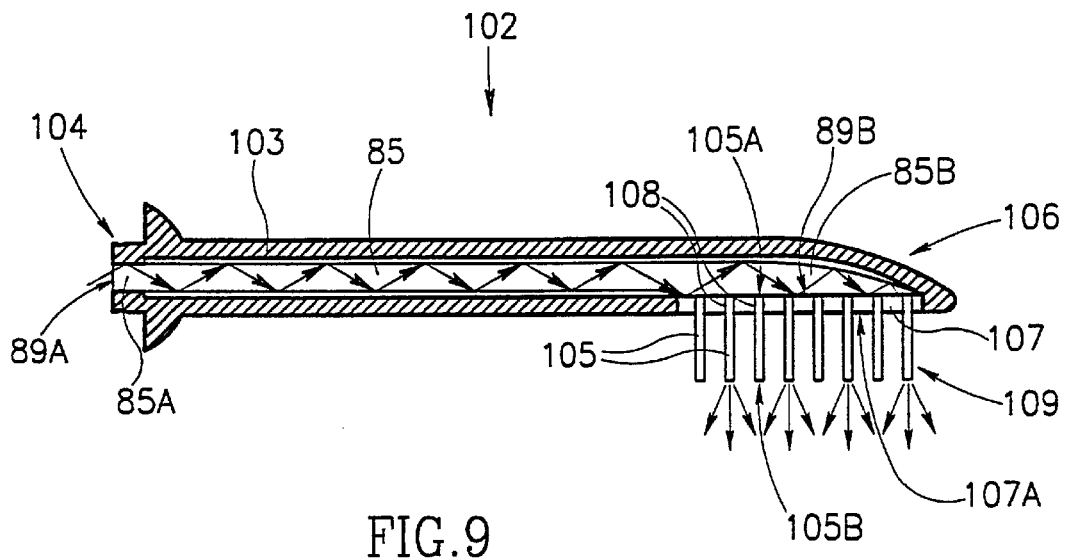
FIG. 9 is a schematic cross sectional view of a toothbrush like light directing member attachable to the handle of the devices of FIGS. 3, 4 and 5, and having transparent bristles optically coupled to a light guide included within the light directing member.

For example, FIG. 9, to which reference is now made, is a schematic cross sectional view of a toothbrush like light directing member 102 attachable to the handle of the devices of FIGS. 3, 4 and 5. Member 102 has transparent bristles 109 optically coupled to a light guide included within the light directing member. Light directing member 102 is an elongated member having a proximal end 104 and a distal end 106. Proximal end 104 can be detachably attached to any of Handles 11, 41 and 61 of FIGS. 3, 4 and 5, respectively. Distal end 106 is insertable into the oral cavity of a user.

light directing member 102 preferably includes a hollow member 103 preferably made from a thermally insulating and light opaque material such as opaque plastic or the like. Light directing member 102 further includes a light guide 85 as described above. Light directing member 102 further preferably includes a terminal part 109. Terminal part 109 preferably includes a plate 107 made of a thermally insulating and preferably light opaque material such as plastic or the like. Terminal part 109 preferably has a plurality of holes 108 passing therethrough.

Terminal part 109 further includes a plurality of transparent bristles 105. Each of the bristles 105 has a first end 105A and a second end 105B. Bristles 105 are attached to plane 107. First end 105A of each of the bristles 105 is inserted into a hole 108 and glued to or frictionally held within the hole. First end 105A of each of bristles 105 is optically coupled to light guide 85 at surface 89B thereof by abutting surface 89B or by being glued to surface 89B using a suitable optically transparent glue.

Second end 105B of each of bristles 105 extends distally from plate 107 in a direction generally perpendicular to a surface 107A thereof. Bristles 106 are preferably made from a flexible material which is transparent to the bandwidth of the band limited light which is being used for photothermally coagulating the oral bacteria. For example, bristles 105 can be made form nylon or from any other suitably transparent flexible plastic. Light from surface 89B enters first end 105A and is guided within each bristle 105, light exiting ends 105B of bristles 105 irradiates the surfaces of the teeth and may photothermally coagulate selectively stained bacteria within plaque covering the surfaces of the teeth.

While all the preferred embodiments of the present invention disclosed hereinabove are useful in photothermally coagulating bacteria within plaque deposited on the more accessible surfaces of teeth, plaque on tooth surfaces which are less accessible to irradiation may need a treatment using another technique of irradiation.

Figure 10:
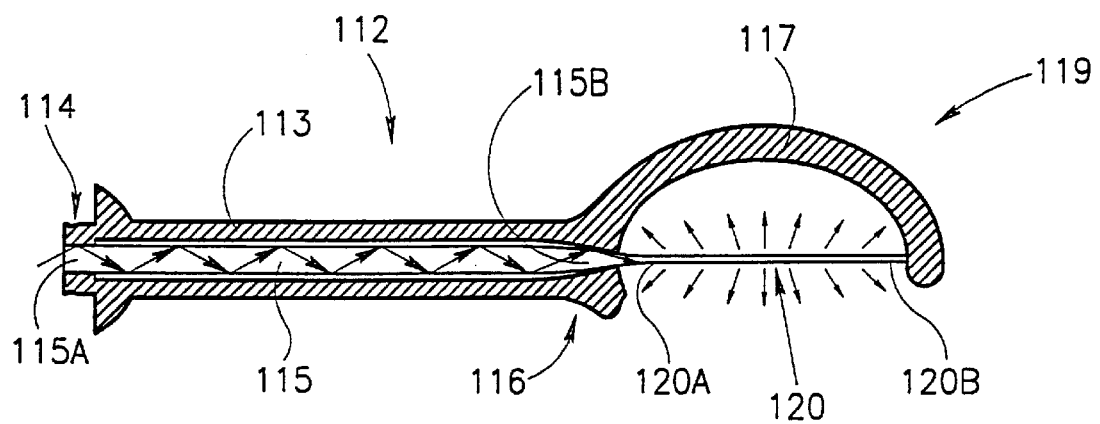
FIG. 10 is a schematic cross sectional view of a light directing member attachable to the handle of the devices of FIGS. 3, 4 and 5, and having a light scattering dental floss member optically coupled to a light guide included within the light directing member.

For example, FIG. 10 to which reference is now made is a schematic cross sectional view of a light directing member 112 in accordance with a preferred embodiment of the invention. It is preferably attachable to the hand held part of the devices of FIGS. 3, 4 and 5 and has a light scattering dental floss like member 120 optically coupled to a light guide 115 included within a hollow cavity member 113 within the light directing member. Light directing member 112 has a proximal end 114 and a distal end 116. Light guide 115 has a first end 115A at proximal end 114 of light directing member 112 and a second narrowing end 115B at distal end.

Light directing member 112 includes a terminal part 119 extending from distal end 116. Terminal part 119 includes a floss holding member 117 holding light scattering dental floss like member 120 having a first part 120A and a second part 120B. Floss like member 120 is preferably made from a flexible transparent material such as nylon or any other type of suitably transparent flexible plastic. First part 120A and a second part 120B. Floss like member 120 is preferably made from a flexible transparent material such as nylon or any other type of suitably transparent flexible plastic. First part 120A is attached to and optically coupled to the second end 115B of the light guide 115. The optical coupling my be performed by a glue having suitable optical properties or, alternatively, floss like member 120 can be an extension of narrowing end 115B of light guide 115. Second part 120B of floss like member 120 is attached to floss holding member 117 such that floss like member is suitably held for flossing.

Floss like member 120 is constructed to scatter light which enters it from light guide 115. The scattering of light may be caused by small light reflecting particles which are embedded in the transparent plastic material forming the floss like member 120. However, other methods of inducing light scattering may also be used such as, for example, forming a plurality of closely spaced grooves or indentations on the outer surface of the floss like member.

After selective staining of plaque bacteria as disclosed above, a user inserts the floss like member 120 between the teeth as he would with ordinary floss. The light scattered from floss like member 120 irradiates the plaque on the surfaces of the teeth that are not accessible by regular brushing and performs photothermal coagulation of selectively stained plaque bacteria positioned at these inaccessible surfaces, while normal flossing is performed It is noted that each of the handles 11, 41 and 61 can be attached to any of the light directing members 22, 82, 92, 102 and 112 of FIGS. 3, 7, 8, 9 and 10, respectively It is further noted that, while any of the light directing members 22, 82, 92, 102 and 112 of FIGS. 3, 7, 8, 9 and 10, respectively, may be made for extended used, they may also be made to be disposable. Furthermore, while various features and forms of features have been shown in the various preferred embodiments, many of these features and variations may be present in other preferred embodiments of the invention. Furthermore, some preferred embodiments of the invention may omit some features shown in the preferred embodiments.

It will be appreciated by those skilled in the art that many variations of the preferred embodiments of the present invention can be made which are within the scope and spirit of the present invention. As used herein, the words "comprise" or "include" or their conjugates mean "including but not necessarily limited to."

What is claimed is:

1. Oral hygiene apparatus for destroying sensitized oral bacteria, comprising:

an incoherent light source, comprising a flash lamp;

a light directing member, adapted for directing light from said light source onto at least part of a surface of at least one tooth within an oral cavity, said light being in an amount and at a wavelength effective to destroy bacteria but not to cause coagulation of blood vessels in the mouth; and a toothbrush like member adjacent to of surrounding said exit port.

2. Apparatus according to claim 1 wherein said light directing member comprises a reflective layer coated light passage.

3. Apparatus according to claim 1 wherein the light directing member comprises a reflective layer coated light passage.

4. Apparatus according to claim 3 wherein said reflective layer coated light passage comprises a hollow passage whose radial extent is defined by a light reflecting surface.

5. Apparatus according to claim 2 wherein said light guide comprises an elongated member, having at least one peripheral surface uncoated by a reflecting material, said light guide directing light entering it at one end by internal reflection from said at least one peripheral surface to a second end.

6. Apparatus according to claim 1 wherein said incoherent light source includes a reflector which directs at least part of the light produced by said lamp to said light directing member.

7. Apparatus according to claim 6 wherein said reflector is a parabolic reflector, a spherical reflector, a quasi-spherical reflector or an ellipsoidal reflector.

8. Apparatus according to claim 6 wherein said light source further includes at least one lens disposed between said flash lamp and said light directing member for directing light onto said light directing member.

9. Apparatus according to claim 1 including at least one filter which passes light to which said bacteria has been sensitized.

10. Apparatus according to claim 9 wherein the at least one filter substantially blocks light at wavelengths at which oxyhemoglobin absorbs substantial energy.

11. Apparatus according to claim 1 wherein said light is directed to said tooth surface from an exit port of the light directing member.

12. Apparatus according to claim 1 wherein said tooth brush like member comprises a plurality of bristle like members arranged peripherally around said exit port to enable said light exiting said port to reach said at least part of a surface of at least one tooth within said oral cavity while teeth are being brushed by said tooth brush like member.

13. Apparatus according to claim 1 and including a power source that powers the incoherent light source and a controller that controls said light source.

14. Apparatus according to claim 13 wherein said power source is a battery and wherein said incoherent light source, said battery and said controller are mounted within a common housing.

15. Apparatus according to claim 1 wherein said light directing member is easily separated from the light source and wherein the light directing member is disposable.

16. Oral hygiene apparatus for destroying sensitized oral bacteria, comprising:
an incoherent light source, comprising a flash lamp;
a light directing member, adapted for directing light from said light source onto at least part of a surface of at least one tooth within an oral cavity, said light being in an amount and at a wavelength effective to destroy bacteria but not to cause coagulation of blood vessels in the mouth; and
a plurality of bristles coupled to said light directing member such that a first end of each of said plurality of bristles is optically coupled to said second end of said light guide and a second end of each of said plurality of bristles extends out of said terminal part for directing at least part of said light onto said at least part of said surface of said at least one tooth within said oral cavity.

17. Oral hygiene apparatus for destroying sensitized oral bacteria, comprising:
an incoherent light source, comprising a flash lamp;
a light directing member, adapted for directing light from said light source onto at least part of a surface of at least one tooth within an oral cavity, said light being in an amount and at a wavelength effective to destroy bacteria but not to cause coagulation of blood vessels in the mouth; and
a dental floss like member optically coupled to said incoherent light source which member emits said light along its length.

18. A method for selective photothermal destruction of bacteria, the method comprising:
selectively staining at least some bacteria by application of a suitable selective bacterial stain; and
exposing at least some of the stained bacteria after said step of selectively staining to pulsed incoherent light produced by a flash lamp, to photothermally coagulate said bacteria.

19. Apparatus according to claim 18 wherein said incoherent light is band limited to exclude a portion of said light having wavelengths which are substantially absorbed by oxyhemoglobin.

20. A method according to claim 18 wherein said pulsed incoherent broad band light has a frequency of pulsing in the range of 0.5–50 pulses per second, a pulse duration in the range of 0.1–10 milliseconds and an energy density in the range of 0.1–10 joule/cm$^2$.

21. A method according to claim 18 wherein said selective bacterial stain has at least one substantial light absorption peak which has no substantial overlap with the major peaks of light absorption of oxyhemoglobin.

22. A method according to claim 18 wherein exposing comprises:
generating at least one pulse of incoherent broad band light from said pulsed light source;
modifying said at least one pulse of light to exclude a substantial portion of said at least one pulse of light, said portion having wavelengths which are substantially absorbed by oxyhemoglobin, to convert said at least one pulse of light into at least one band-limited light pulse; and
directing said at least one band-limited light pulse onto said bacterial to photothermally coagulate said bacteria.

23. A method according to claim 18 wherein the bacteria are oral bacteria.

24. A method according to claim 23 wherein the bacteria are situated in the oral cavity.

25. An oral hygiene kit comprising:
a substance including a stain for bacteria in a concentration sufficient to stain at least some bacteria remaining in the mouth; and
an oral hygiene apparatus comprising:
a light source which generates polychromatic radiation which is absorbed by the stain; and
a light directing member, adapted for directing light from said light source onto at least part of a surface of at least one tooth within an oral cavity, said light being in an amount and at a wavelength effective to destroy bacteria, in conjunction with said substance but not to cause coagulation of blood vessels in the mouth.

26. An oral hygiene kit according to claim 25 wherein the oral hygiene apparatus comprises:
an incoherent light source, comprising a flash lamp; and
a light directing member, adapted for directing light from said light source onto at least part of a surface of at least one tooth within an oral cavity, said light being in an amount and at a wavelength effective to destroy bacteria but not to cause coagulation of blood vessels in the mouth.

27. A kit according to claim 25 wherein bacteria stained with said stains have a substantial absorption peak at a wavelength for which oxyhemoglobin does not have such an absorption peak.

28. A kit according to claim 25 wherein the stain comprises E-127 (Erythrosin-B).

29. A kit according to claim 25 wherein the substance is comprised in a dentifrice and wherein said bacteria remain stained after tooth brushing with the dentifrice.

30. A kit according to claim 29 wherein the stain in contained in the dentifrice in a weight percentage of 0.1% . 1%.

31. Oral hygiene apparatus for destroying sensitized oral bacteria, comprising:
an incoherent light source;
a light directing member, adapted for directing light from said light source onto at least part of a surface of at least one tooth within an oral cavity, said light being in an amount and at a wavelength effective to destroy bacteria but not to cause coagulation of blood vessels in the mouth, wherein said light is directed to said tooth surface from an exit port of the light directing member; and including a dental floss like member optically coupled to the said incoherent light source which member emits light along its path.

32. A method for selective photothermal destruction of bacteria, the method comprising:

selectively staining at least some bacteria by application of a suitable selective bacterial stain; and exposing at least some of said stained bacteria after said step of selectively staining to incoherent light, to photothermally coagulate said bacteria, wherein said incoherent light is band limited to exclude a portion of said light having wavelengths which are substantially absorbed by oxyhemoglobin.

33. A method for selective photothermal destruction of bacteria, the method comprising:

selectively staining at least some bacteria by application of a suitable selective bacterial stain; and exposing at least some of said stained bacteria after said step of selectively staining to incoherent light, to photothermally coagulate said bacteria, wherein said incoherent broad band light is pulsed and wherein said pulsed incoherent broad band light has a frequency of pulsing in the range of 0.5–50 pulses per second, a pulse duration in the range of 0.1–10 milliseconds and an energy density in the range of 0.1–10 joule/cm$^2$.

34. A method for selective photothermal destruction of bacteria, the method comprising:

selectively staining at least some bacteria by application of a suitable selective bacterial stain; and exposing at least some of said stained bacteria after said step of selectively staining to incoherent light, to photothermally coagulate said bacteria, wherein exposing comprises:

generating at least one pulse of incoherent broad band light from a pulsed light source including a gas discharge lamp or a flash lamp;

modifying said at least one pulse of light to exclude a substantial portion of said at least one pulse of light, said portion having wavelengths which are substantially absorbed by oxyhemoglobin, to convert said at least one pulse of light into at least one band-limited light pulse; and directing said at least one band-limited light pulse onto said bacteria to photothermally coagulate said bacteria.

* * * * *